Figure 1:
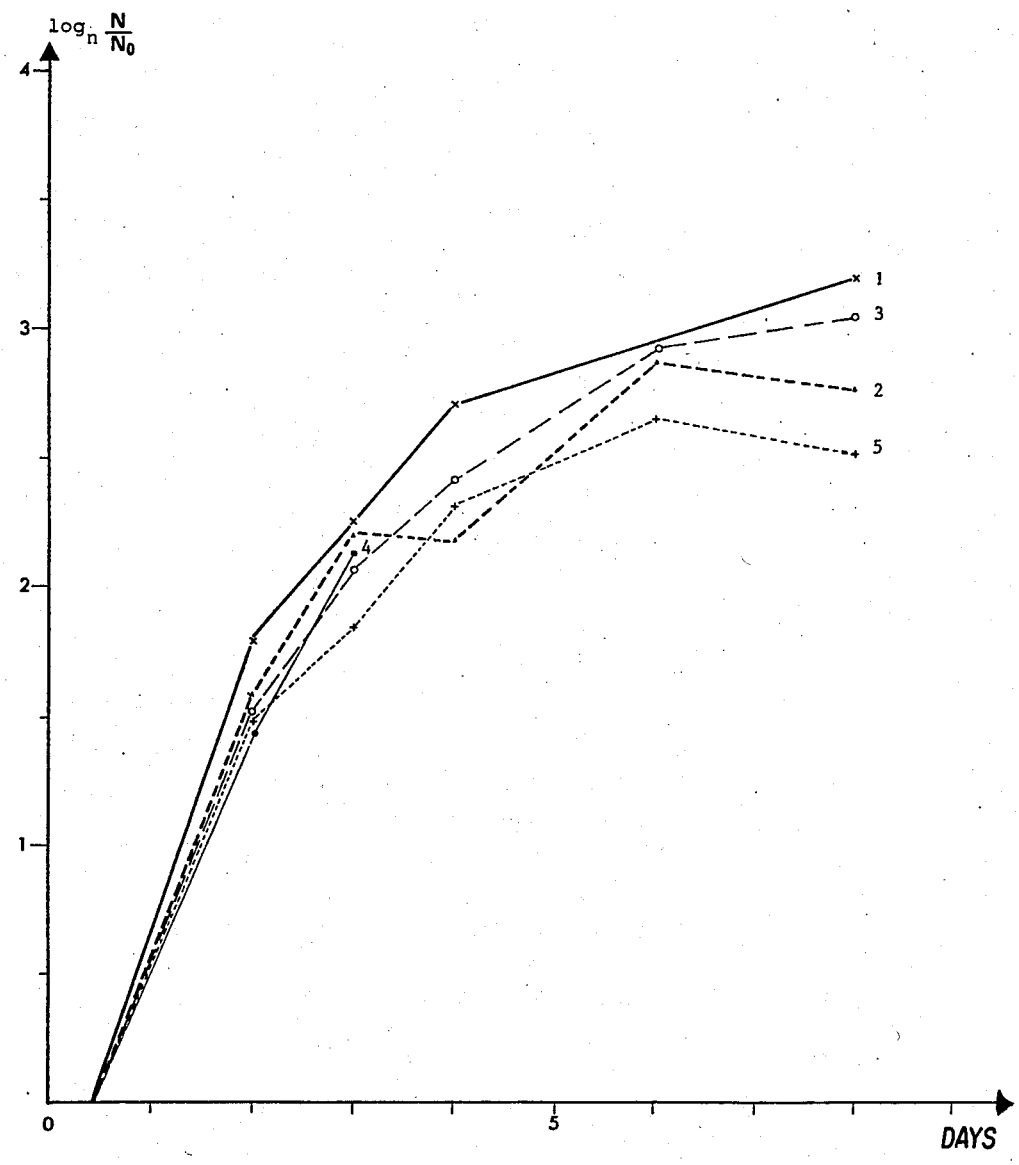

United States Patent [19]

Chessebeuf et al.

[11] Patent Number: 4,786,599

[45] Date of Patent: Nov. 22, 1988

[54] SERUM-FREE ANIMAL CELL CULTURE MEDIUM AND METHODS FOR THE PRIMARY CULTURE AND PRODUCTION OF CELL LINES USING THIS MEDIUM

[75] Inventors: Martina L. Chessebeuf, Dijon; Prudent H. Padieu, Chevigny St Sauveur, both of France

[73] Assignee: Institut National de la Sante et de la Recherche Medicale, Paris, France

[21] Appl. No.: 684,334

[22] PCT Filed: Mar. 23, 1984

[86] PCT No.: PCT/FR84/00080

§ 371 Date: Nov. 21, 1984

§ 102(e) Date: Nov. 21, 1984

[87] PCT Pub. No.: WO84/03710

PCT Pub. Date: Sep. 27, 1984

[30] Foreign Application Priority Data

Mar. 24, 1983 [FR] France ............................ 83 04843

[51] Int. Cl.$^4$ ............................ C12N 5/00; C12R 1/91
[52] U.S. Cl. ............................ 435/240.31; 435/240.3; 435/948
[58] Field of Search ............. 435/240, 241, 172.2, 435/948

[56] References Cited

U.S. PATENT DOCUMENTS

| Re. 30,985 | 6/1982 | Cartaya | 435/241 |
|---|---|---|---|
| 4,036,693 | 7/1977 | Levine et al. | 435/241 |
| 4,440,860 | 4/1984 | Klagsbrun | 435/240 |

FOREIGN PATENT DOCUMENTS

| 0060565 | 9/1982 | European Pat. Off. | 435/240 |
|---|---|---|---|
| 0076647 | 4/1983 | European Pat. Off. | 435/240 |

OTHER PUBLICATIONS

Kaighn, M. Edward, "Human Liver Cells", *Tissue Culture Methods and Applications*, Kruse, Jr., and Patterson, Jr. Ed., Academic Press, New York, 1973, pp. 54–58.
Maciag et al., "Hormonal Requirements of Baby Hamster Kidney Cells in Culture", *Cell Biology International Reports*, vol. 4(1), 1980, pp. 43–50.

*Primary Examiner*—John E. Tarcza
*Attorney, Agent, or Firm*—Larson and Taylor

[57] ABSTRACT

A serum-free animal tissue culture medium contains a mixture of six fatty acids and albumin or dextran. The medium is particularly adapted for the primary culture of rat liver epithelial cells and possibly in the presence of hormones and/or growth factors, for obtaining cell lines, in particular of myelomae and hybridomae.

20 Claims, 4 Drawing Sheets

SERUM-FREE ANIMAL CELL CULTURE MEDIUM AND METHODS FOR THE PRIMARY CULTURE AND PRODUCTION OF CELL LINES USING THIS MEDIUM

The invention relates to animal cell culture media.

It relates more particularly to a synthetic medium for animal cell culture, particularly of epithelial cells or myeloma cells and their hybrids of hybridoma type, not containing serum and suitable both for primary culture of animal cells, and for production of cell lines from this primary culture or from another. It also relates to a primary culture process and a process for producing an animal cell line using such a medium.

For a certain number of years, intensive research has been carried out in order to perfect a culture medium enabling hepatic cell lines to be obtained having the characteristics of parenchymal hepatocytes, in order particularly to elucidate the regulatory mechanisms which control the proliferation and differentiation of hepatic cells.

Until now two types of hepatic cell cultures have been widely developed from cells obtained after dissociation of hepatic tissue by means of collagenase or trypsin.

It is known that the digestion of liver by collagenase provides non-proliferating parenchymal hepatocytes which can be kept several days, even several weeks, either in a culture medium supplemented with serum (Serum-Supplemented Medium: SSM), or in a culture medium without serum (Serum-Free Medium: SFM). These parenchymal cells manifest various functions of liver and consequently advantageously replace liver homogenates or tissue slices. However, the inevitable senescence of these hepatocytes does not allow long-term studies, which has prompted researchers to develop proliferating cultures of hepatic epithelial cells. Such cultures have been, in a first phase, obtained in media supplemented with serum (SSM), after digestion of hepatic tissue with trypsin or from primary cultures initiated after collagenase digestion. Although the growth of normal hepatic epithelial cells generally presents difficulties, particularly by reason of a too considerable development of fibroblastic cells, it has been possible to show that proliferating cultures of hepatic epithelial cells possess characteristics of hepatic parenchymal cells. However, the addition of serum to the culture medium introduces into the latter a very large number of components among which are particularly final products and effectors, that is to say regulators of the liver metabolisms which complicate, even render impossible, the use of cell lines obtained in serum-supplemented media, in particular in the case of certain studies such as those related to the biosynthesis of cholesterol, of neutral bile sterols and of bile acids.

To remedy, at least in part, the various drawbacks presented by cell lines obtained in serum-supplemented culture media, various authors have proposed replacing the serum by hormones and growth factors such as in particular insulin and "epidermal growth factor", whose presence until now was considered as indispensable for the development of cell lines.

Now, the dependence of numerous metabolic processes of liver with respect to hormones is well known. In consequence, the presence of hormones in the culture medium leads also to modifications or disturbances, even in certain cases to the impossibility of carrying out reliable studies on hepatic cell lines obtained in hormone-supplemented culture media.

In the case of the industrial use of established epithelial cell lines and of myeloma lines and their hybrids of the hybridoma type, the presence of serum or of unknown or poorly defined components leads to a great difficulty even to an impossibility, of purifying the one or more cell biology products for purposes of administration to man. In addition, the non-definition of the composition of the medium leads to prohibition of such human utilization of these biological products by the international and national health authorities (OMS, FDA, Ministry of Health, etc.).

The purpose of the invention is to provide an animal cell culture medium not presenting the drawbacks of known culture media.

Now it has been observed surprisingly and against all expectation, that it is possible to carry out both primary cultures and secondary cultures in a medium containing neither serum, and in the majority of cases nor hormones, nor growth factors, by supplementing it, in well defined proportions, with certain fatty acids or other esters in the presence of a lipophile biopolymer in an amount capable of permitting the dissolution of the added fatty acids or of their esters.

One of the objects of the invention is hence a culture medium of the above indicated type containing neither serum, and in the majority of cases nor hormones, nor growth factors, characterized in that it is supplemented, in certain well defined proportions, with certain fatty acids or their esters, in the presence of lipophile biopolymer in an amount capable of permitting the dissolution of the added amount of fatty acids or of their esters.

In its most general aspect the invention therefore provides an animal cell culture medium devoid of serum, characterized by the use of a basic medium containing the nutrients indispensable for the growth of animal cells and of certain fatty acids or their esters, at relative concentrations and at an overall concentration adapted to ensure the growth of said cells, these concentrations having not to exceed a threshold beyond which these fatty acids or their esters would become toxic with respect to the cell cultures. It is moreover self-evident that the fatty acids used, or their esters, must have a concentration greater than a minimum threshold to permit the growth of animal cells.

A more particular object of the invention is a serum-free animal cell culture medium, characterized in that it is essentially constituted by:

(a) a synthetic basal medium designed for animal cell culture;

(b) 0.05 to 30 $\mu$eq/l of fatty acids constituted by a mixture of compounds selected from among palmitic acid, cis-palmitoleic acid, stearic acid, cis-oleic acid, cis-linoleic acid and cis-linolenic acid and their esters, present in the following proportions, with respect to the free fatty acid:
from 0.0155 to 24.0 $\mu$mole/l of palmitic acid;
from 0.0058 to 9.0 $\mu$mole/l of cis-palmitoleic acid;
from 0.0014 to 2.0 $\mu$mole/l of stearic acid;
from 0.0067 to 10.0 $\mu$mole/l of cis-oleic acid;
from 0.0178 to 27.0 $\mu$mole/l of cis-linoleic acid; and
from 0.0028 to 4.0 $\mu$mole/l of cis-linolenic acid, adsorbed on (c) at least one lipophile biopolymer present in an amount capable of ensuring the dissolution of the fatty acids or of their esters present in the medium.

In a preferred embodiment, the invention relates to a serum-free animal cell culture medium, characterized in that it is essentially constituted by:

(a) a basic synthetic medium designed for animal cell culture;

(b) from 0.05 to 15 μeq/l of fatty acids constituted by a mixture of compounds selected from among palmitic acid, cis-palmitoleic acid, stearic acid, cis-oleic acid, cis-linoleic acid and cis-linolenic acid and their esters, present in the following proportions related to the free fatty acid:

from 0.0155 to 4.65 μmole/l of palmitic acid;
from 0.0058 to 1.74 μmole/l of cis-palmitoleic acid;
from 0.0014 to 0.42 μmole/l of stearic acid;
from 0.0067 to 2.01 μmole/l of cis-oleic acid;
from 0.0178 to 5.34 μmole/l of cis-linolenic acid; and
from 0.0028 to 0.84 μmole/l of cis-linolenic acid; adsorbed on (c) at least one lipophile biopolymer present in an amount which can ensure the dissolution of the fatty acids or of their esters present in the medium, this medium being essentially devoid of hormones and growth factors.

According to another preferred embodiment, the invention relates to an animal cell culture medium, particularly of liver epithelial cells, serum free, characterized in that it is essentially constituted by:

(a) a basic synthetic medium designed for animal cell culture;

(b) 2 to 30 μeq/l of fatty acids constituted by a mixture of compounds selected from among palmitic acid, cis-palmitoleic acid, stearic acid, cis-oleic acid, cis-linoleic acid, and cis-linolenic acid and their esters, present in the following proportions, related to the free fatty acid:

from 0.0155 to 24.0 μmole/l of palmitic acid;
from 0.6 to 9.0 μmole/l of cis-palmitoleic acid;
from 0.0014 to 2.0 μmole/l of stearic acid;
from 0.5 to 10.0 μmole/l of cis-oleic acid;
from 1.2 to 27.0 μmole/l of cis-linolenic acid; and
from 0.3 to 4.0 μmole/l of cis-linolenic acid, adsorbed on (c) at least one lipophile biopolymer present in an amount which can ensure the dissolution of the fatty acids or of their esters present in the medium, this medium being essentially devoid of hormones and growth factors.

Whatever the dilution of the fatty acids used or of their esters in the culture medium, it has proved advantageous to use them in the following molar propotions:

palmitic acid: 31.0%
cis-palmitoleic acid: 11.6%
stearic acid: 2.8%
cis-oleic acid: 13.4%
cis-linoleic acid: 35.6%
cis-linolenic acid: 5.6%

According to a preferred embodiment of the invention, the medium comprises in addition a non-cytotoxic concentration, throughout the passage of the culture, of an antibiotic, preferably of wide spectrum. Preferably there is used, as antibiotic, gentamicin in the proportion of 25 to 100 mg/l.

According to another preferred embodiment of the invention, free fatty acids are preferably used.

The lipophile biopolymer is preferably constituted by a polymolecular polysaccharide containing α-glucopyrannose units, known under the common name of dextran, preferably in an amount of 0.5 to 200 mg/l of culture medium or by lipid-free or not lipid-free albumin, preferably in an amount of 2 to 6 g/l of culture medium.

Equivalent results being obtained with lipid-free albumin on the one hand, and with not lipid-free albumin, on the other hand, it seems that the lipids contained at the start in albumin do not take part in the proliferation process of the cells. Under these conditions, taking into account the lesser cost of not-lipid-free albumin, it is very particularly preferred.

As synthetic basal medium it is possible advantageously to resort to a synthetic medium used customarily for the culture of animal cells, such as particularly:

Ham media
Waymouth MB 752/1 medium
RPMI 1629 and 1640 media
Eagle medium
modified Eagle media
Williams E medium
199 medium and the derived media of the types
MEM and
MEMα.

Particularly good results have been obtained with the medium marketed under the reference "Ham F 10 medium" by the Gibco Company, Grand Island, N.Y., U.S.A., whose composition will be indicated below and the Williams E medium characterized by a greater richness in vitamins.

If the culture medium contains one or several of the above mentioned fatty acids, or their esters, account must be taken in the calculation of the overall concentration of the fatty acids.

In certain particular cases such as particularly the culture of myeloma cells and their hybrids of the hybridoma type, it may prove useful, even necessary, to add to the culture medium hormones and/or growth factors customarily used in cell cultures. By way of indication, it is possible to resort to hormones and/or growth factors selected from among those mentioned by D. Barnes and G. Sato. in Anal. Biochem. (1980), 102, 235–270 and to use them at the doses indicated in this article.

Another object of the invention is constituted by a process of primary culture of animal cells, using such a medium.

The primary culture process according to the invention comprises essentially the steps consisting of:

(1) taking up the tissue containing the cells to be cultivated and mincing it very finely, in a basal culture medium, preferably in the basal medium which has to be used but containing $Ca^{2+}$ and $Mg^{2+}$ ions, warmed (30°–37° C.), under aseptic conditions, (2) after rinsing, preferably in the basal medium which has to be used but not containing $Ca^{2+}$ and $Mg^{2+}$ ions, subjecting the tissue to enzymatic digestion, (3) transferring the suspension of cells thus freed into a basal medium, preferably that used for the culture, centrifuging whilst pursuing in parallel the digestion of the remaining tissue, (4) placing the centrifugation pellet in suspension in the culture medium according to the invention containing as the case may be a surfactant for the culture substratum then, (5) inoculating the suspension thus obtained on the culture substratum previously or simultaneously surfacted, (6) incubating in a sealed incubator, saturated with water vapor, in the presence of a mixture of nitrogen, oxygen and carbon dioxide in proportions useful in biology of cell respiration, whilst periodically renewing the culture medium, the steps (3) to (6) being repeated on different fractions of dissociated desired cells, obtained successively in step (2), using each time a new culture substratum.

The enzymatic digestion is carried out by means of a proteolytic enzyme such as collagenase or preferably trypsin, if necessary associated with other enzymes acting on the complex saccharides, such as hyaluronidase and/or upon the polynucleic acids, such as DNA-ase and RNA-ase, by a method known in itself, for example that described by M. Chessebeuf et al. in Biochemie, 56, 1365-1379 (1974).

The volume of culture medium added in step (4) corresponds in practice to the inner volume of the vessel containing the culture substratum which has to be used in step (5).

As culture substratum, recourse may be had particularly to any dish customarily used for the culture of animal cells, such as a Petri dish or, preferably, a Cooper dish or again to spherical culture microcarriers.

The surfacting of the substratum seems to have the role of permitting "anchorage" of the cells and thus facilitating their proliferation. It may be carried out before the seeding, by usual methods, known to the technicians skilled in the art, for example by means of serum, collagen, polylysine or fibronectin. Various types of serums, preferably foetal calf serum or newborn calf serum which is less expensive, may be used for this purpose.

After the surfacting, the substratum being rinsed several times, preferably with the basal medium used, before seeding, there only remain on the substratum the elements which have to serve for the "anchorage" of the cells, whereas, in the case of serum, the constituents which are active on cell growth are removed.

The surfacting can also be carried out simultaneously with the culture, particularly by means of the presence of fibronectin in the culture medium.

Another object of the invention is a process for producing an animal cell line using the culture medium according to the invention. This process is characterized by the fact that it comprises essentially the steps consisting of:

(a) subjecting to enzymatic digestion the cellular product of a prior culture, particularly primary, having preferably reached confluence, to initiate one or several secondary culture(s), (b) carrying out the one or more secondary culture(s) in the culture medium according to the invention and (c) repeating steps (a) and (b) as many times as is necessary to preserve the cell line for the desired time.

The invention will be better understood by means of the detailed examples described below. It is self-evident that these examples are purely for the purpose of illustrating and better explaining the invention, without in any way limiting the scope of the same.

EXAMPLE 1

Culture of Epithelial Cells from Rat Liver

Culture Medium:

The basal medium is obtained from Ham medium in powder marketed under the reference "Ham F 10 medium" by the Gibco Company, Grand Island, N.Y., U.S.A. After dissolving in triple distilled water, it has the following composition:

| Components | mg/l | Components | mg/l |
|---|---|---|---|
| L-alanine | 9.000 | L-inositol | 0.541 |
| L-arginine HCl | 211.000 | Nicotinamide | 0.615 |
| L-asparagine H$_2$O | 15.010 | Pyridoxine HCl | 0.206 |
| L-aspartic acid | 13.000 | Riboflavine | 0.376 |
| L-cysteine | 25.000 | Thiamine HCl | 1.000 |
| L-glutamic acid | 14.700 | Vitamin B12 | 1.360 |
| L-glutamine | 146.000 | CaCl$_2$ 2H$_2$O | 44.000 |
| Glycine | 7.510 | CuSO$_4$ 5H$_2$O | 0.0025 |
| L-histidine HCl H$_2$O | 23.000 | FeSO$_4$ 7H$_2$O | 0.8340 |
| L-isoleucine | 2.600 | KCl | 285.000 |
| L-leucine | 13.000 | KH$_2$PO$_4$ | 83.000 |
| L-lysine HCl | 29.000 | MgSO$_4$ 7H$_2$O | 153.000 |
| L-methionine | 4.480 | NaCl | 7400.000 |
| L-phenylalanine | 5.000 | Na$_2$HPO$_4$ | 153.700 |
| L-proline | 11.500 | NaHCO$_3$ | 1200.000 |
| L-serine | 10.500 | ZnSO$_4$ 7H$_2$O | 0.0288 |
| L-threonine | 3.570 | Glucose | 1100.000 |
| L-tryptophane | 0.600 | Hypoxanthine | 4.680 |
| L-tyrosine (disodium salt) | 2.620 | Lipoic acid | 0.200 |
| L-valine | 3.500 | Phenol red | 1.200 |
| Biotin | 0.024 | Sodium pyruvate | 110.000 |
| Ca D-pantothenate | 0.715 | Thymidine | 0.700 |
| Choline chloride | 0.698 | Triple distilled water ad | 1000 ml |
| Folic acid | 1.320 | | |

To this medium are added 50 mg/l of gentamicin and the free fatty acids used according to the invention, marketed by the NU CHECK PREP. Company, ELYSIAN, MN are added, at a total concentration of fatty acids of 7.6 μeq/l, in the following molar proportions:

palmitic acid: 31.0%
cis-palmitoleic acid: 11.6%
stearic acid: 2.8%
cis-oleic acid: 13.4%
cis-linoleic acid: 35.6%
cis-linolenic acid: 5.6% these acids being adsorbed on 4 g/l of albumin (No1 4503 of the Sigma Company, Saint Louis, MO, U.S.A.).

Primary Culture of Rat Liver Epithelial Cells:

The livers of 8 newborn rats, preferably of the same sex, are excised and minced finely under aseptic conditions. After two rinses in "Ham F 10 medium" not containing however Ca$^{2+}$ and Mg$^{2+}$ ions, the finely minced livers are transferred to a trypsinization bottle of 50 ml, provided with a magnetic stirrer. To them is added an equal volume of a solution diluted 3 times by the trypsin rinsing medium 1:250 (that is to say trypsin which hydrolyses 250 times its weight of casein) coming from the Microbiological Associates Company, Bethesda, MD, U.S.A. It is stirred for 10 minutes at 100 rpm, at 37° C., then the suspension of cells is decanted into "Ham F 10 medium" cooled with ice (2 volumes of medium per volume of cells) and it is centrifuged at 30 g. In parallel, the trypsinization solution is renewed in the bottle.

The sequential digestion with the trypsin is repeated as long as the digestion yield is maintained (viable epithelial cells identified by microscope), that is to say in general 6 to 9 times.

Each configuration pellet comprising about 10$^5$ viable epithelial cells is suspended in about 4.3 ml of the culture medium according to the invention, described above, and inoculated in 1 Cooper dish (No. 3009 of the Falcon Company, Oxnard, CA. U.S.A.) surfaced with serum. The dishes are kept at 37° C. in a sealed culture incubator (Lequeux, Paris, France) saturated with water vapour, in the presence of a nitrogen, oxygen and carbon-dioxide mixture at 76%:19%:5%. The culture medium is changed every two days.

The surfacting of the dishes is done by means of fetal or newborn calf serum by incubation overnight at 37° C. After throwing out the serum, it is rinsed twice with "Ham F 10 medium" warmed (30°-37° C.), before the inoculation.

A little after the inoculation, the epithelial cells are attached in the form of numerous monolayer sheets composed of 100 to 500 cells each. The growth of these areas leads to confluent cultures of a pure population of epithelial cells of $10^6$ cells per dish in less than 8 days, on the average after 6 days for a surface area of 20 cm².

It is striking to note the inaptitude of the culture medium according to the invention to promote growth of fibroblastoid and endothelial cells. The culture medium according to the invention hence leads to a cellular selection by promoting a privileged growth of epithelial cells.

Cell Propagation:

When the primary cultures have appreciably reached confluency, the contents of each dish is treated with the trypsin solution used previously for the digestion of the liver and seeded in secondary culture to initiate two new cultures.

The culture medium according to the invention enables the successful carrying out of the primary cultures and of the secondary cultures as far as a high number of passages (positive results have still been obtained at the end of 80 passages).

Study of the Hepatic Functions of Epithelial Cells of Liver Obtained According to the Invention:

To evaluate the qualities of the epithelial liver cells obtained according to the invention, there was studied on those cells, functions characteristic of the liver with respect to the metabolism of endogenic compounds, namely the inducibility of L-tyrosine aminotransferase by glucocorticoids, the biosynthesis of bile acids and the metabolism of progesterone.

Results Obtained

A. Activity of L-tyrosine aminotransferase (TAT) and its induction or inducibility by glucocorticoids The well-known induction of the enzyme TAT (EC 2.6.1.5) by glucocorticoids in vivo was demonstrated for the first time in 1957; it is often used to prove the maintenance of an hepatic activity in liver culture systems.

The activity of TAT and its inducibility by glucocorticoids ($10^{-6}$ mole/l of dexamethasone (dex) over 5 hours at 37° C.) have been studied in hepatic epithelial cell lines obtained according to the invention by following the technique described by T. I. Diamondstone in Anal. Biochem. 16, 395-401 (1966) and by comparing with the induction obtained in vivo in post-natal rat liver. The study was done on five lines of epithelial cells of liver obtained according to the invention. Two lines (54C ♂ 5FRS and 54C(D) ♂ 5FRS) were studied from the eighth passage up to the 28th passage, two others (45A ♂ 6FRS and 45A(D) ♂ 6FRS) from the 8th or respectively the 14th passage, up to the 30th passage. The following Table I shows the evolution of the induction ratio as a function of the progression of the number of passages. The induction ratios were principally comprised between 1.5 and 2.1 in the first passages for the two lines 54C and 45A. These induction ratios then started to diminish to come back to 1 around the 15th passage for the line 54C and around the 25th passage for line 45A. The lines 54C(D) and 45A(D) maintained an induction ratio higher than 1 respectively up to the 25th passage for the first and up to the 30th passage for the second.

In conclusion, the lines obtained according to the invention have shown that they have had a basal activity of TAT corresponding to 20 to 30% of that of the liver in vivo in the case of rats of the same age, but that the induction ratio was about 75% of that observed in vivo, under the same conditions.

TABLE I

| Expression of the inductibility of TAT by glucocorticoids | | | | | | | |
|---|---|---|---|---|---|---|---|
| 54C ♂ 5 FRS | | 54C(D) ♂ 5 FRS | | 45A ♂ 6 FRS | | 45A(D) ♂ 6 FRS | |
| 8.7 ± 3.7 | | 7.3 ± 4.3 | | 5.6 ± 3.3 | | 6,5 ± 2.8 | |
| P n° | I/B | P n° | I/B | P n° | I/B | P n° | I/B |
| 8 | 1.5 | 8 | 1.6 | 8 | 1.7 | — | — |
| 12 | 1.5 | 12 | 1.3 | 14 | 2.0 | 14 | 2.5 |
| 15 | 1.8 | — | — | 18 | 1.2 | 18 | 1.7 |
| 19 | 0.7 | 18 | 2.1 | 21 | 1.4 | — | — |
| 25 | 1.0 | 25 | 1.2 | 24 | 1.5 | 24 | 1.7 |
| 28 | 1.1 | 28 | 0.8 | 30 | 1.1 | 30 | 1.3 |

1st line: reference of the cell line;
2nd line: average ± coefficient of variation of the basal activity of TAT for each cell line:
3rd line: P No = number of passage and I/B = inducibility ratio, that is to say activity after induction/basal activity.

The specific activity of TAT is expressed in mU/mg of protein. One unit is the amount of enzyme forming 1 nmole of p-hydroxyphenyl pyruvate per minute at 37° C. Each value represents the average of two tests. The enzymatic activity and the protein content were determined by using three culture dishes with a monolayer of cells either for the control or for the induction by dexamethasone (dex) ($10^{-6}$ mole/l for 5 hours at 37° C.). The cells were collected after double rinsing with 2 ml of cold PBS (phosphate saline buffer) then rubbing with 2 ml of PBS and were immediately separated in the form of a centrifugation pellet before storage at $-30°$ C. After thawing, the cells were placed in the presence of a total volume of 1 ml of buffer (0.1M potassium phosphate, pH 7.6, 1 mM EDTA, 0.2 mM pyridoxal phosphate and 5 nM Na ketoglutarate). The resulting suspension was centrifuged at 40,000 g for 30 minutes before examining the enzymatic activity.

B. Biosynthesis of the Bile Acids

Chenode-oxycholic acid and cholic acid are the two principal bile acids (BA), so-called primary bile acids synthesized by the liver of most animal species, whilst in the rat liver there occurs a particular primary bile synthesis, the biosynthesis of α-muricholic acid. This is a production specific to murine species which corresponds to an hydroxylation at the 6β position of chenode-oxycholic acid.

The biosynthesis of free bile acids was investigated in cell lines obtained according to the invention.

1. Biosynthesis of Cholic and Chenode-oxycholic Acids

This study was carried out on SFM cell line obtained according to the invention, on the 11th passage. The bile acids were extracted from the culture medium and analyzed by gas phase chromatography and by gas chromatography coupled to mass spectrometery. The chromatographic trace and the analysis of the mass spectra noted have shown that the line studied on the 11th passage synthesized, under the conditions of the study, cholic acid and chenode-oxychlolic acid. The mass spectra were quite in agreement with those of the standards. This method enabled calculation of the amount of the bile acids synthesized, expressed in nanograms per 24 hours and per mg of cultured cells. This synthesis level was 11.4 nanograms in the case of free chenode oxycholic acid and 63 nanograms in the case of free cholic acid.

It will be recalled, for comparison, that in the case of the in vivo rat liver it was demonstrated that the total synthesis of primary bile acids (chenode-oxycholic and cholic acids), whether free or conjugated, was of the order of 280 nanograms per 24 hours and per mg of fresh liver.

2. Biosynthesis of α-muricholic Acid

Another line was studied at the 9th passage by incubating with radioactive chenode-oxycholic acid labeled with carbon 14 ($^{14}C$) at the 24 position. This dihydroxylated bile acid was hydroxylated at the 6 position, in the 6β isomer, to give rise to α-muricholic labeled at the 24 position by carbon 14. The level of α-muricholic acid synthesized was of the order of 100 nanograms per 24 hours and per mg of cultivated cells. This value is quite comparable with the value found in vivo in the rat.

These observations on the biosynthesis of the bile acids show pertinently that rat liver epithelial cells cultivated in the culture medium according to the invention can maintain in activity the hydroxylases of the steroid ring which are microsomal enzymes dependent on cytochrome P450. These hydroxylases which permit the synthesis of cholic acid and chenode-oxycholic acid belong to the class of cytochrome P450 acting on endogenic compounds, whilst 6β-cholanoylhydroxylase which converts chenode-oxycholic acid into α-muricholic acid is a cytochrome P450 hydroxylase which acts on exogenic compounds, of the class which take part in the biotranformation of xenobiotics.

Thus, there has been demonstrated the biosynthesis of bile acids by the liver epithelial hepatic cell lines obtained by means of the culture medium according to the invention. This observation could not have been made on cell lines containing serum. In fact it is known that the bile acids are inhibitors of their own biosynthesis hence, in the case of cultures of liver epithelial cells obtained in a medium containing serum, normally the bile acids which are present in the serum inhibit the biosynthesis of bile acids by the liver cells.

Thus, due to the liver cell culture in the medium according to the invention it has been possible to establish pertinently the biosynthesis of bile acids. In addition, these liver cells being rat liver cells, It has been possible to establish the maintenance in culture of a specific characteristic of the rat liver, namely the synthesis of α-muricholic acid.

C. Metabolism of progesterone

The metabolism of progesterone shown below diagramatically has been verified on two epithelial hepatic cell lines from non pubescent rats from the 4th to the 7th passage.

Progesterone labeled with carbon 14 at the 4 position has been incubated to a physiological level (62–80 nmoles/l) during 24 hours at confluency.

The steroid extract of each passage has been thin layer chromatographed and the radioactivity of the fractions separated on each plate was measured by means of a radioactivity counter.

This study has shown that 87% of the precursor had been metabolised in four fractions containing respectively pregnanetriols, 20 α-dihydroprogestrone and pregnanediols, pregnanolones, containing residual progesterone, and pregnanedione.

Each fraction obtained by thin layer chromatography was analysed and quantified by gas phase chromatography associated with mass spectrometry. The presence of 11 metabolites shown in the following diagram has thus been demonstrated.

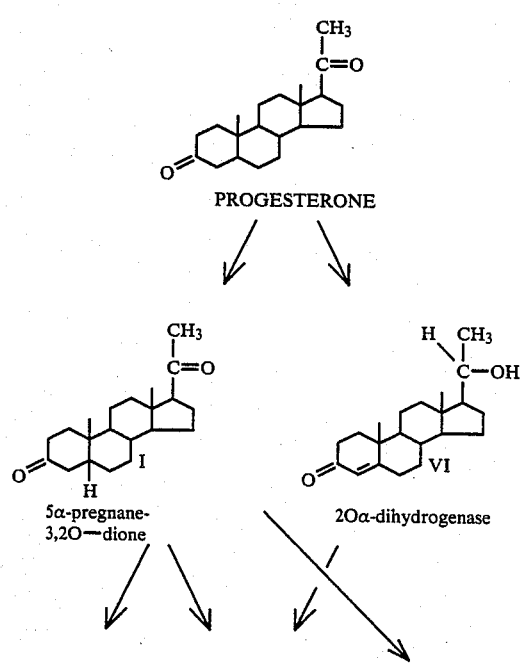

-continued

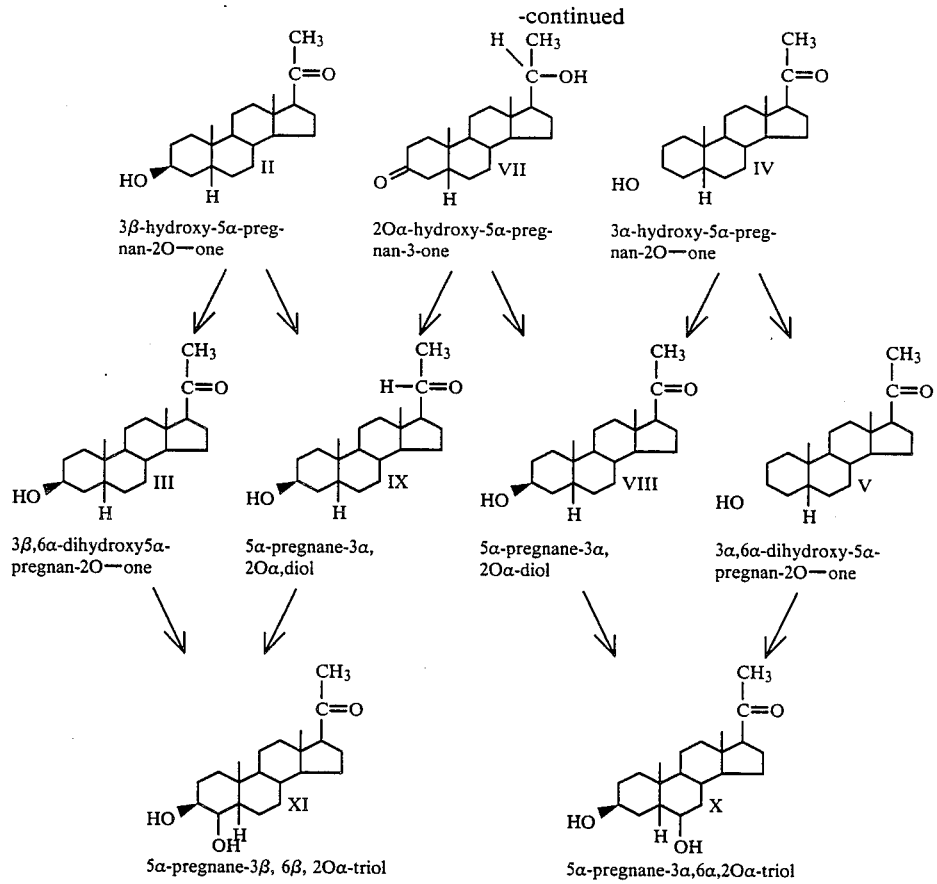

The most striking metabolic characteristics of the liver have been found in these cultures, namely:

20α reduction of the C₂₀-oxo group (compounds VI to XI);

production of pregnanediolones (compounds IV and V) and of pregnanetriols (compounds X and XI) due to 6α-pregnanolone hydroxylase, which enzyme is a specific marker of the liver;

unique presence of the reduction at the 5α position of the Δ₄₋₅ double bound (compounds I to V and VII to XI) without any 5β reduction, and preeminence of 3α oxido-reduction.

The appearance of these metabolites of progesterone constitutes the normal phenotypic expression of the metabolism of progesterone in non pubescent rats (and also in adult female rats).

In conclusion: the culture of liver epithelial cells in the culture medium according to the invention offers a novel tool for studying the expression and regulation of hepatic functions in cells not undergoing the disturbing effects of serum or of hormones.

EXAMPLE 2

Culture of monkey kidney epithelial cells by using a dextran as lipophile biopolymer; propagation of the VERO line General indications:

The VERO line is a normal kidney epithelial cell line of the Cercopithecus aethiops monkey, established in March, 1962 by Y. YASAMURA at the University of Chiba in Japan and deposited in the American Type Culture Collection under no. ATCC CCL81. The cell strain used comes from a flask of VERO IM 153 obtained on Apr. 24, 1983 on the 153th passage and is derived from the specimen coming from the ATCC.

This strain is divided into two sub-lines, one sub-line is propagated normally in 199 medium (Morgan et al. Proc. Soc. Exp. Biol. Med. (1950). 73. 1) supplemented with 5% of fetal calf serum (SSM) and called VERO 1, VERO 2 . . . VERO 15 line progressively with the passages in SSM and the other sub-line is propagated in serum free medium (SFM) containing albumin and fatty acids, described in example 1, and this in dishes surfacted by means of serum according to the method described in example 1.

After three passages of the sub-line growing in SFM, a sub-line is initiated in a new serum-free culture medium wherein the lipophile biopolymer of albumin type is replaced by a lipophile biopolymer of dextran type (Pharmacia, France) highly purified, without heavy metals, chemically and structurally defined, at levels of 2 to 50 mg/l, whilst maintaining the proportion of the six fatty acids used according to the invention, indicated in example 1 but with a final total concentration of 0.152 μeq/l adsorbed on the dextran. The serum-free and vector protein-free medium or SPFM ("Serum- and Protein-Free Medium") is used as such to propagate the VERO S1, VERO S2 . . . VERO S14 (S for synthetic) line. The culture of the VERO S line in SFM containing albumin is stopped.

The SPFM can if necessary be used with the addition of hormones and growth factors. As way of indication it is possible to use the hormones and growth factors mentioned by G. Sato et al. In Anal. Biochem. (1980) 102: 235–270, at the doses indicated in this article.

It is possible besides to replace the surfacting of the substratum by the serum by adding to the SPFM fibronectins of different origins as proteins of attachment as well as other proteins and polypeptides of attachment such as collagens, polylysins.

The various polymers of isomeric chains of ($\alpha 1\rightarrow 3$)-D-glucopyranosides crosslinked by ($\alpha 1\rightarrow 6$)-D-glucopyranosyl groups and which constitute the homogene dextrans such as the dextrans of molecular weights 10,000, 40,000, 50,000, 70,000, 500,000, and 2,000,000 and the charged dextrans such as dextran sulfate and DEAE-dextran, distinguished by their average molecular weight, charges or groups, can be used according to the invention as lipophile biopolymer. Dextran of molecular weight 500,000 and still more dextran of molecular weight 2,000,000 called dextran T2000 (trade name) use however is preferred. For convenience, the selected dextran, preferably dextran T2000, is dissolved in a mother solution 50 to 100 times more concentrated in the basal synthetic medium (BSM: "Basal Synthetic Medium") in order to facilitate storage at +4° C. after sterilizing filtration.

The cell propagation is effected on each subculture according to the method of isolation and seeding of the cells described in example 1.

The surfacting of the dishes is carried out according to the method indicated in example 1 by using the serum available, for example of fetal calf, newborn calf, adult bovine, horse or human.

The final medium is prepared by conventional techniques, from a BSM. Preferably a relatively rich BSM such as for example 199 medium, MEMα medium (C. P. Stanners et al., Nature, New Biol. (1971) 230: 310) with or without the presence of the conventional 4 ribosides and 4 deoxyribosides (pentosides) and Williams E medium (G. M. Williams et al. Exp. Cell Res. (1971) 69: 105) or any other enriched BSM is selected. To this BSM are added the one or more selected antibiotics, then the sterile stock solution of the dextran T2000 to reach the desired concentration, and to finish, after having sterilized the medium by filtration, the sterile stock solutions of fatty acids whilst rendering complete the dissolution by the action of ultrasound for some minutes, then in the last place if necessary the selected hormones and growth factors in sterile stock solution.

Below are given the compositions of the 199 medium and of the Williams E medium.

| Components | Medium 199 199 with Earle salts mg/l | 199 with Hanks salts mg/l |
|---|---|---|
| L-alanine | 25.00 | 25.00 |
| L-arginine HCl | 70.00 | 70.00 |
| L-aspartic acid | 30.00 | 30.00 |
| L-cystein HCl | 0.099 | 0.099 |
| L-cystine | 23.66 | 23.66 |
| L-glutamic acid | 66.82 | 66.82 |
| L-glutamine | 100.0 | 100.0 |
| Glutathion | 0.05 | 0.05 |
| Glycocolle | 50.00 | 50.00 |
| L-histidine HCl H$_2$O | 21.88 | 21.88 |
| L-hydroxyproline | 10.00 | 10.00 |
| L-isoleucine | 20.00 | 20.00 |
| L-leucine | 60.00 | 60.00 |
| L-lysine HCl | 70.00 | 70.00 |
| L-methionine | 15.00 | 15.00 |
| L-phenylalanine | 25.00 | 25.00 |
| L-proline | 40.00 | 40.00 |
| L-serine | 25.00 | 25.00 |
| L-threonine | 30.00 | 30.00 |
| L-tryptophane | 10.00 | 10.00 |
| L-tyrosine | 40.00 | 40.00 |
| L-valine | 25.00 | 25.00 |
| L-ascorbic acid | 0.05 | 0.05 |
| Biotin | 0.01 | 0.01 |
| Calciferol | 0.10 | 0.10 |
| Ca D-pantothenate | 0.01 | 0.01 |
| Choline chloride | 0.50 | 0.50 |
| Folic acid | 0.01 | 0.01 |
| I-inositol | 0.05 | 0.05 |
| Menadione | 0.019 | 0.019 |
| Nicotinic acid | 0.025 | 0.025 |
| Nicotinamide | 0.025 | 0.025 |
| P-aminobenzoic acid | 0.05 | 0.05 |
| Pyridoxal HCl | 0.025 | 0.025 |
| Pyridoxine HCl | 0.025 | 0.025 |
| Riboflavine | 0.01 | 0.01 |
| Thiamine HCl | 0.01 | 0.01 |
| α-tocopherol | 0.01 | 0.01 |
| Disodium Phosphate | | |
| Vitamin A | 0.0115 | 0.115 |
| CaCl$_2$ 2H$_2$O | 264.9 | 185.5 |
| Fe(NO$_3$)$_3$ 9H$_2$O | 0.10 | 0.10 |
| KCl | 400.0 | 400.0 |
| KH$_2$PO$_4$ | | 60.00 |
| MgSO$_4$ 7H$_2$O | 200.0 | 200.0 |
| NaCl | 6800 | 8000 |
| NaHCO$_3$ | 2200 | 350.0 |
| NaH$_2$PO$_4$ 2H$_2$O | 158.3 | |
| Na$_2$HPO$_4$ | | 47.50 |
| Adenine | 10.00 | 10.00 |
| 5'-AMP | 0.20 | 0.20 |
| ATP, sodium salt | 10.00 | 10.00 |
| Cholesterol | 0.20 | 0.20 |
| 2-Deoxyribose | 0.50 | 0.50 |
| Glucose | 1000 | 1000 |
| Guanine HCl | 0.30 | 0.30 |
| Hypoxanthine | 0.30 | 0.30 |
| Ribose | 0.50 | 0.50 |
| Sodium acetate | 36.71 | 36.71 |
| Phenol Red | 17.00 | 17.00 |
| Thymine | 0.30 | 0.30 |
| Tween 80 | 5.00 | 5.00 |
| Uracil | 0.30 | 0.30 |
| Xanthine | 0.30 | 0.30 |

| Williams E Medium | | | |
|---|---|---|---|
| Components | mg/l | Components | mg/l |
| L-alanine | 90.00 | Choline chloride | 1.50 |
| L-arginine HCl | 60.50 | Folic acid | 1.00 |
| L-aspargine H$_2$O | 20.00 | I-inositol | 2.00 |
| L-aspartic acid | 30.00 | Menadione | 0.01 |
| L-cysteine HCl | 52.05 | Nicotinamide | 1.00 |
| L-cystine | 23.70 | Pyridoxal HCl | 1.00 |
| L-glutamic acid | 50.00 | Riboflavine | 0.10 |
| L-glutamine | 292.0 | Thiamine HCl | 1.00 |
| Glutathion | 0.05 | DL-α-tocopherol (phosphate) | 0.01 |
| Glycine | 50.00 | Vitamin A | 0.10 |
| L-histidine HCl H$_2$O | 20.30 | Vitamin B12 | 0.20 |
| L-isoleucine | 50.00 | CaCl$_2$ 2H$_2$O | 264.9 |
| L-leucine | 75.00 | CuSO$_4$ 5H$_2$O | 0.00009 |
| L-lysine HCl | 87.50 | Fe(NO$_3$)$_3$ 9H$_2$O | 0.0001 |
| L-methionine | 15.00 | KCl | 400.0 |
| L-phenylalanine | 25.00 | MgSO$_4$ 7H$_2$O | 200.0 |
| L-proline | 30.00 | MnCl$_2$ 4H$_2$O | 0.0001 |
| L-serine | 10.00 | NaCl | 6800 |
| L-threonine | 40.00 | NaHCO$_3$ | 2200 |
| L-tryptophane | 10.00 | NaH$_2$PO$_4$ 2H$_2$O | 158.3 |
| L-tyrosine | 35.00 | ZnSO$_4$ 7H$_2$O | 0.0002 |
| L-valine | 50.00 | Glucose | 2000 |
| L-ascorbic acid | 2.00 | Methyl Linoleate | 0.03 |
| Biotin | 0.50 | Phenol Red | 10.00 |
| Calciferol | 1.00 | Sodium pyruvate | 25.00 |
| Ca D-panthothenate | 1.00 | | |

Results:

VERO line, VERO S subline, is maintained for 16 passages in the basal SPFM (BSPFM) prepared as follows from:

a chemically defined synthetic medium, the Williams BSM E, which is preferred because it contains all the vitamins including vitamin A and vitamin C (it may be replaced by any other medium of the same type, 199 or MEMα, with or without pentosides), completed with the required proportions of L-glutamine according to the form of presentation, medium in powder or liquid medium and/or of bicarbonate according to the percentage of $CO_2$, 5% or 10%, mixed with the atmospheric air of the culture incubator; ultrapure water corresponding to the standards ASTM-1 [ASTM D-1193-70, Annual Book of ASTM-Standards (1970)] or better water purified by the method of Chessebeuf et al. [C.R. Soc. Biol. Paris (1979), 173, 469-582] and
one or more of wide spectrum antibiotics, preferably gentamicin in the proportion of 50 mg/l.

At this level of preparation the medium is filtered in sterile conditions and stored at 4° C. for a period not exceeding about 10 days on account of the degradation of the L-glutamine.

At the time of use, the following compounds are added extemporaneously:
sterile stock solution of dextran T2000 stored at +4° C. to obtain the preferred concentration of 10 mg/l;
sterile ethanolic stock solution of fatty acids stored at 4° C. to obtain the preferred final concentration of 152 nanoequivalents (nEq)/liter containing the six free fatty acids used according to the invention, in the proportions indicated in example 1.

First Series of Tests: Effect of Addition of Hormones or Growth Factors

In the BSPFM so prepared, used alone or with the addition of hormones or growth factors, the VERO line is cultivated to the 15th passage by carrying out surfacing with fetal calf serum (SVF) and the growth (number of cells) is studied as a function of time.

Composition of culture media:
medium 1: BSPFM alone
medium 2: BSPFM+insulin: 1.25 mg/l
medium 3: BSPFM+transferrin-iron (saturated or half-saturated with iron): 10 mg/l
medium 4: BSPFM+"epidermal growth factor" EGF: 12.5 μg/l
medium 5: BSPFM+insulin: 1.25 mg/l+transferrin-iron: 10 mg/l+EGF: 12.5 μg/l.

The five media ensure growth from an inoculum of 500,000 to 700,000 cells (viability 98 to 100%) per dish of 20 cm², ending in a cellular confluency ratio comprised between $4 \times 10^6$ and $5.25 \times 10^6$ cells per 20 cm² at the sixteenth day after seeding. At the eighth day after seeding the best results are obtained with media 1 and 3. The ratio of cells is $4.9 \times 10^6$ cells/20 cm² for medium 1 and $5.7 \times 10^6$ cells/20 cm² for medium 3. The cell multiplication ratio in medium 1 is 9.8 and the time of doubling of the cell population is 19 h 35 min. For medium 3, the cell multiplication ratio is 7.2 and the time of doubling the cell population is 25 h 15 min.

FIG. 1 is a graphical drawing of the results obtained in this test. It comprises an ordinate in neper logarithms, $\log_n N/No$, where N is the number of cells at time t and No the number of cells at time t=0 corresponding to counting carried out 12 h after inoculation. The numbers of the graphs correspond to the numbers of the media concerned. The five inoculums proliferate identically. There is noted however a certain superiority of medium 1. One of the cultures (medium 4) was stopped on the third day.

Still within the framework of this first series of tests, there is studied the influence of other hormones and growth factors on the growth of the VERO S15 line in culture dishes surfaced with SVF.

The media used are:
medium 1: without hormone or growth factor (as previously); cell multiplication ratio: 8.8; time of doubling of the cell population: 21 h 49 min;
medium 4: (as previously) with EGF: 12.8 μg/ml; cell multiplication ratio: 9.8; time of doubling of the cell population: 19 h 35 min.;
medium 5: BSPFM of medium 1+MSA (stimulating activity factor of the multiplication: "Multiplication Stimulating Activity"): 1 μ/l; cell multiplication ratio: 6.5; time of doubling of the cell population: 29 h 32 min.;
medium 6: BSPFM of medium 1+dexamethasone: 50 μg/l; cell multiplication ratio: 6.5; time of doubling of the cell population: 29 h 32 min.;
medium 7: BSPFM of medium 1+putrescine: 100 μmoles/l; cell multiplication ratio: 8.2, time of doubling of the cell population: 23 h 25 min.

It is observed that only the growth factor EGF slightly increases the cell multiplication ratio whilst another hormone, dexamethasone, and the MSA cell growth factor do not contribute a great improvement with respect to the medium BSPFM. Putrescine contributes a stimulation but then causes a toxic reaction at the time of confluency. Used in another experiment at a ratio 10 times weaker, 10 μmoles/l, putrescine does not contribute a difference with respect to the control medium BSPFM.

Figure 2:
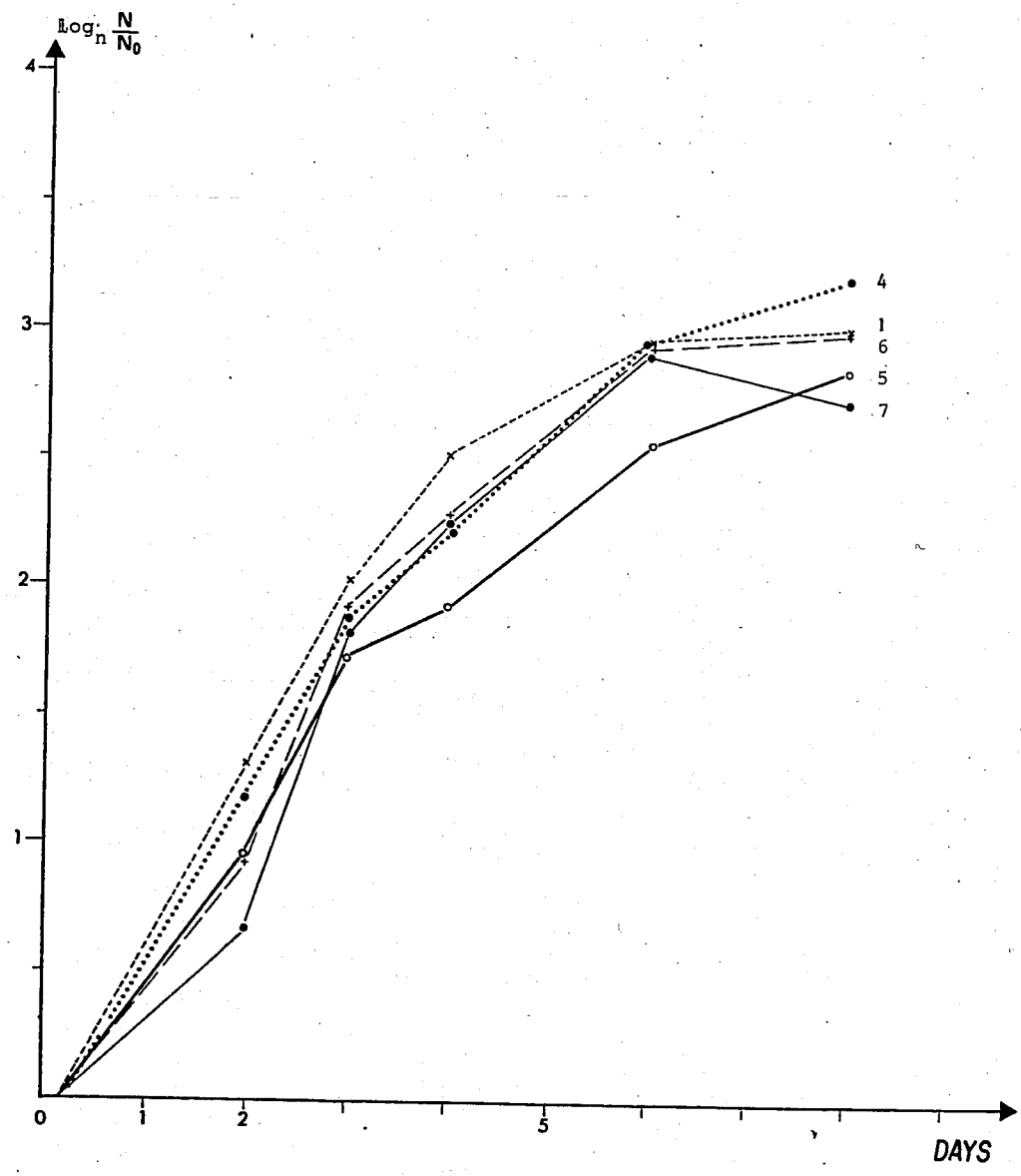

FIG. 2 gives a graphical representation, of the same type as FIG. 1, of the results obtained with the above media 1, 4, 5, 6 and 7.

This representation shows well the negative effects of MSA and putrescine the absence of effect of dexamethasone and the slightly stimulating effect of EGF with respect to the effect of BSPFM on cell growth. For industrial production of the VERO S line, the addition of EGF to the BSPFM composed of BSM, Williams E medium, gentamicin: 50 mg/l+dextran T2000: 10 mg/l+6 fatty acids used according to the invention: 152 nEq/l, does not contribute an economically advantageous improvement.

Second Series of Tests: Culture on SSM (comparative tests):

There is studied, at the 16th passage, the growth of the VERO 15 line in SSM containing 5% serum from the first passage coming from the VERO IM 153 line, after division into two sub-lines subcultivated into two different BSMs in the presence of 5% of serum:
medium 1: Williams E BSM+gentamicin: 50 mg/l+5% of fetal calf serum (SVF)
medium 2: BSM constituted by 50% of 199 and 50% of MEMα without pentosides+gentamicin: 50 mg/l+5% of SVF.

The confluency is reached in both cases in six days with an average ratio of $4.1 \times 10^6$ cells/20 cm² for an initial inoculum of $0.5 \times 10^6$ cells. The cell multiplication ratio is hence 8.5 in 6 days, and the time of doubling the cell population is 17 h.

No difference is observed between the two types of BSM when they are completed with SVF type serum.

Third Series of Tests: Influence of BSM in the Case of a Culture on SPFM

There is studied the cell growth of the VERO S17 line, 17th passage in the two SPFM corresponding to the two BSM of the second series of tests, namely the E medium of Williams on the one hand and the mixture of 50% of the medium 199 and 50% of MEMα medium without pentosides, in the absence of serum and of proteins, for two cultures conducted in parallel in culture dishes of 20 cm² of surfaced surface area either by SVF, or by replacing the surfacting with serum by the addition of human fibronectin (FH) to the medium. These media are:

medium 1: Williams BSM E+gentamicin: 50 mg/l+dextran T2000: 10 mg/l+6 fatty acids: 152 nEq/l; surfacting of the substratum with SVF.

medium 2: identical with medium 1 but with the addition to the medium of FH: 9 μg/20 cm², namely 2 μg/ml of SPFM (without surfacting with serum).

medium 3: BSM composed of 50% of 199 and 50% of MEMα pentosides+gentamicin: 50 mg/l+dextran T2000: 10 mg/l+6 fatty acids: 152 nEq/l; surfacting by SVF.

medium 4: identical with medium 3, but with the addition of FH: 2 μg/ml (without surfacting with serum).

Starting from an inoculum of 363,000 cells, the culture of the VERO S17 line carried out in the SPFM medium composed of Williams BSM E (media 1 and 2) shows a better proliferation than the VERO 15 line in the presence of serum (second series of tests) since after 6 days the number of cells is situated at an average of $4.9 \times 10^6$ cells/20 cm², corresponding to a cell multiplication ratio of 13.5 and the time of doubling the cell population is 14 h 13 min. for the VERO S17 line against the respective values of 8.5 and 17 h for VERO 15 line growing in the same Williams BSM E supplemented with 5% of serum.

The two homologous cultures carried out in the BSM constituted of a mixture in equal proportions of medium 199 and medium MEMα reach the growth plateau after 4 days for a number of cells of the VERO S17 line ranging from $2.25 \times 10^6$ to $2.35 \times 10^6$ cells/20 cm². The ratio of cell multiplication is 3.3 and the time of doubling the cell population is 29 h.

This example shows the importance of the choice of BSM in the case of the serum-free culture.

Figure 3:
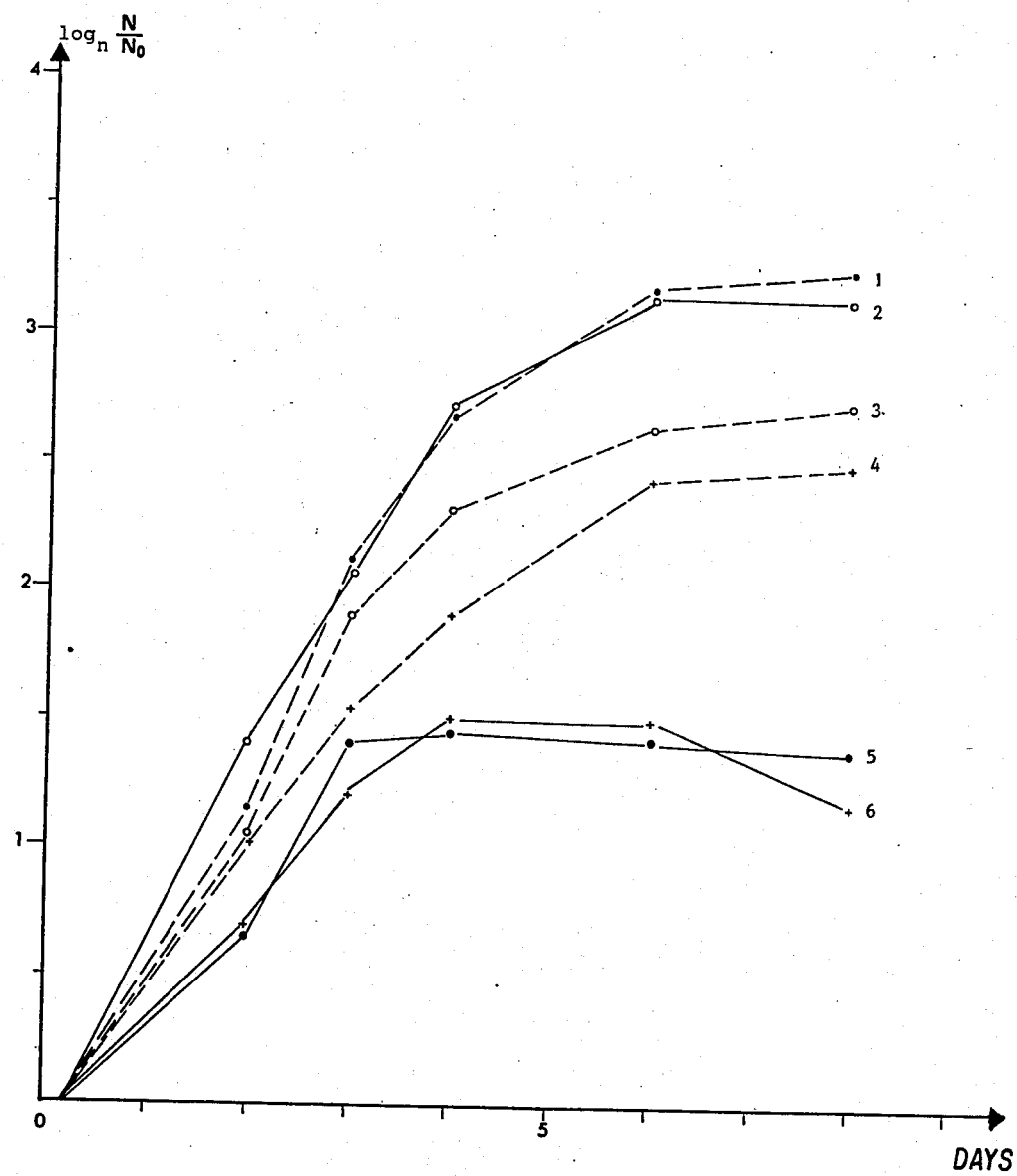

FIG. 3 combines in a single graph the results of the second and third series of tests represented semilogarithmically where the ordinate is the neper logarithm $log_n N/No$, for N=number of cells at time t and No=number of cells at time $t_o$. This $t_o$ corresponds in fact to the counting 6 h after seeding.

This figure enables the comparison on the one hand of the type of BSM (Williams E medium or 50% of medium 199+50% of medium MEMα without pentosides), entering into the composition of the SSM with 5% of fetal calf serum or SPFM, and on the other hand the method of anchoring the cells of SPFM culture, either by surfacting with SVF incubated alone 12 h in the dish then rejected with subsequent rinsing, or by addition to the SPFM of FH in the ratio of 2 mg/l without any other preparation of the substratum before subcultivation. The numbers of the curved correspond to the numbers of the culture media with the composition:

medium 1: BSM: Williams E+gentamicin: 50 mg/l+5% of SVF medium 2: BSM: 50% of 199+50% of MEMα without pentosides+gentamicin: 50 mg/l+5% of SVF medium 3: BSM: Williams E+gentamicin: 50 mg/l+dextran T2000: 10 mg/l+6 fatty acids: 152 nEq/l; surfacting with SVF medium 4: BSM: Williams E+gentamicin: 50 mg/l+dextran T2000: 10 mg/l+6 fatty acids: 152 nEq/l+FH: 2 mg/l; without any other surfacting medium 5: BSM: 50% of 199+50% of MEMα without pentosides+gentamicin: 50 mg/l+dextran T2000: 10 mg/l+6 fatty acids: 152 nEq/l; surfacting with SVF medium 6: BSM: 50% of 199+50% of MEMα without pentosides+gentoamicin: 50 mg/l+dextran T2000: 10 mg/l+6 fatty acids: 152 nEq/l+FH: 2 mg/l, without any other surfacting.

FIG. 3 demonstrates the deficiency of the BSM mixture constituted by 50% of medium 199+50% of medium MEMα without pentosides. This deficiency is not compensated by the composition of the SPFM. The problem of the cell anchorage on the substratum does not come into it since in the case of the four SPFM cultures, the surfacting with SVF or the addition of FH to the medium without other surfacting leads to comparable cell growths in a same group of BSM (media 3 and 4, or media 5 and 6). In the case of SPFM constituted by Williams E BSM, the cell growths (media 3 and 4) remain close to those of the cultures in the presence of serum (media 1 and 2).

Fourth Series of Test: Effect of the Size of the Inoculum

Three comparisons were carried out with the lines VERO S15, VERO S17 and VERO 15;

(i) between two ratios of cells on seeding, either 23,000 cells/cm², or 42 500 cells/cm² in culture dishes of 20 cm², (ii) between Williams E BSM containing serum for the VERO line growing in serum from 1962 and on the 15th passage in the laboratory (VERO 15) and the SPFM medium from the same Williams E BSM, (iii) between two passages of the VERO line growing in SPFM from either 15 passages: VERO S15, or 17 passages: VERO S17.

Description of the Tests and Results:

Medium 1: Williams E BSM+gentamicin 50 mg/l+dextran T2000: 10 mg/l+6 fatty acids: 152 nEq/l; surfacting with SVF; passage VERO S17;

Inoculum 42.500 cells/cm², namely 850,000 cells/20 cm² cell multiplication ratio: $5.7 \times 10^6/850,000 = 6.7$ doubling time of the cell population: $192/6.7 = 28$ h 40 min Medium 2: same BSM as previously: surfacting with SVF; passage VERO 15; Inoculum 23,500 cells/cm², namely 470,000 cells/20 cm²; cell multiplication ratio: $4.95 \times 10^6/470,000 = 10.5$; doubling time of cell population: $192/10.5 = 18$ h 17 min.

Medium 3: same BSM as previously; surfacting with SVF; passage VERO S15; Inoculum 42,500 cells/cm², namely 850,000 cells/20 cm²; cell multiplication ratio: $5.25 \times 10^6/850,000 = 6.6$; doubling time of cell population: $192/6.6 = 29$ h 4 min.

Medium 4: same BSM as previously; surfacting FH; passage VERO S17; Inoculum 23,700 cells/cm², namely 474,000 cells/20 cm²; cell multiplication ratio: $4.9 \times 10^6/474,000 = 10.4$; doubling time of cell population: $192/10.4 = 18$ H 34 min.

Medium 5: same BSM as previously+gentamicin 50 mg/l+5% of SVF; passage VERO 15; Inoculum 23,500 cells/cm², namely 470,000 cells/20 cm²; cell multiplication ratio: $4.9 \times 10^6/470,000 = 10.4$; time of doubling the cell population: $192/10.4 = 18$ h 28 min.

The effect of the size of the inoculum is the same, whether this is in the culture in the presence of SVF or in SPFM cultures: media 1 and 3 or media 2 and 4.

In the case of an inoculum of 23,500 cells/cm², in spite of the presence of serum (medium 5), the cell growth is not more active than in the case of the corresponding SPFM medium (medium 2) and does not catch up in number of cells, the growth of an inoculum of 42,500 cells/cm² in the SPFM media (media 1 and 3).

This study permits the observation that for inoculation ratios of the order of 500,000 cells/20 cm², the SPFM is characterized by the following culture parameters: ratio of cell multiplication 10.5 and time of doubling the cell population 18 h 17 min., similar to those obtained in SSM with 5% serum, respectively 10.4 and 18 h 28 min. At higher inoculation ratios of 850,000 cells/20 cm², the parameters in the case of two SPFM cultures in parallel are similar.

EXAMPLE 3

Growth of the Myeloma SP2/O-Ag-14 Line

The myeloma line of the mouse SP2/O-Ag-14 [M. Shulman et al., Nature (1978), 276, 269–270] is very much used for obtaining hybridomas of myelomatous cells and lymphocytes of animals immunized against one or several antigens in order to obtain one or more hybridoma lines each secreting a monoclonal antibody.

The growth of the line SP2/O-Ag-14 and of the hybridomas secreting monoclonal antibodies which have come therefrom is carried out at present in a medium containing 10% of serum. The addition of serum is responsible for the presence of heterospecific antibodies belonging to the animal species from which it has been taken. These foreign antibodies contaminate the monoclonal antibody secreted by the hybridoma. In fact, the secretion ratio of a monoclonal antibody of a hybridoma is situated mostly between 5 and 100 mg of specific antibody per liter of medium. According to the ratio of the foreign immunoglobulins introduced by the serum added in the proportion of 10% to the culture medium, the contamination is situated between 700 and 1400 mg/l of these foreign antibodies. It is however possible to make hybridoma cells grow in a serum-free medium and often in the presence of albumin in order to obtain a culture medium of which the major immunoglobulin is the monoclonal specific antibody, with respect to other proteins secreted by the hybridoma, to proteins coming from cell lysis, and to proteins which can be added to the culture medium as vector, hormonal, bonding or growth factors.

The growth of the myeloma line of the mouse SP2/O-Ag-14 in SPFM culture media is studied.

The growth of the myeloma line SP2/O-Ag-14 is carried out in culture flasks of 25 cm² surface area. Penicillin, 50 U/ml, and streptomycin, 50 μg/l, customarily used, are used here also in order not to introduce an additional modification factor into the culture method. The cultures are carried out in the absence of surfacting by SVF but by adding FH or SPFM. The SPFM is composed of BSM MEMα without pentosides.

The media used have the following compositions (the cell counts are given in 10⁶ cells):

medium 1: standard culture medium of myeloma cells: RPMI 1640+glucose at 5.6 g/l=Na pyruvate: 1 mmole/l+10% of SVF. Cell multiplication ratio (TMC): 6.3/1.05=6.0; time of doubling the cell population (TDPC): 83/6.0=13 h 30 min.

medium 2: same medium as preceding one where RPMI is replaced by MEMα without pentosides. TMC: 6.3/1.17=5.4; TDPC: 83/5.4=15 h 25 min.

medium 3: BSM MEMα without pentosides+glucose at 5.6 g/l+dextran T2000: 10 mg/l+6 fatty acids: 152 nEg/l,+insulin: 2 mg/l+transferrin-iron: 2 mg/l+EGF: 20 μg/l; TMC: 3.88/0.95=4.1; TDPC: 83/4.1=20 h 19 min.

medium 4: same complete SPFM as that of medium 3+FH: 10 mg/l; TMC: 5.16/1.06=4.9; TDPC: 83/4.9=17 h 3 min.

medium 5: same complete SPFM as that of medium 3+("endothelial cell growth supplement" ECGS): 60 mg/l; TMC: 5.59/1.25=4.5; TDPC: 83/4.5=18 h 34 min.

medium 6: same SPFM as medium 5+FH: 10 mg/l TMC: 5.9/1.0=5.9; TDPC: 83/5.9=14 h 10 min.

The number of cells counted takes into account the cells which are not anchored on the substratum and cells suspended in the medium. The anchorage of the cells to the substratum is faster, and the proliferation is initiated sooner, in media 1 and 2 containing serum.

Medium 3 shows that without FH and without ECGS, the growth appears faster at the start, similar to that of media 1 and 2. In fact few cells are anchored to the substratum, the cells are divided especially in suspension without passing through the attachment phase and die. Media 4 and 5 ensure a similar growth approaching that in SSM due to the presence of FH (medium 4) or of ECGS alone (medium 5 a little more active than medium 4). They improve the stimulation of growth with respect to medium 3, but especially bring back the cell mortality to that of media 1 and 2 by permitting very good anchorage of the cells to the substratum. When the two factors FH and ECGS are added together in medium 6, cell growth is still more effective and approaches that of media 1 and 2 containing serum. It should be recalled that the substratum: has not undergone in the case of SPFM (media 3 to 6) any physicochemical surfacting by the serum or natural or artificial anchorage polymers. Hence in the absence of serum for anchorage of cells, there is produced in the case of media 4, 5 and 6 a latency time corresponding to the anchorage period ensured by cells themselves on the substratum. Nonetheless, the resumption of cell growth occurs at the same time, at 35 h, as in the case of media 1 and 2 containing serum, accelerating strongly in media SPFM 4, 5 and 6 from the 75th hour, to result at the 83rd hour in cell population ratios in these cultures close to ratios in media 1 and 2 in the presence of serum.

The confluency reached for the various cultures in the presence of serum (media 1 and 2) or in the medium SPFM 4 and especially 5 and 6 corresponds to a number of cells between 5 and 7.10⁶ cells/20 cm² in 5 ml of medium.

EXAMPLE 4

Growth of a Hybridoma Obtained from Animal Lymphocytes Immunized Against a Viral Rotavirus Antigen The rotaviruses are responsible for diarrheal disorders dependent or independent of diseases of malnutrition in man as in certain animal species. The availability to the doctor of an etiological diagnosis is an important advantage. It can be done effectively by means of specific antibodies of the various viral strains.

The example given corresponds to the growth of a hybridoma SP2/O-Ag-14 of the Rotavirus Rota IV-21.

The usual culture medium in the presence of serum is BSM RPMI 1640+glucose at 5.6 g/l+Na pyruvate: 1 mmole/l. This medium may be replaced by Williams E BSM. In this example, the growth of this hybridoma was produced in the latter BSM+glucose at 5.6 g/l+gentamicin: 50 mg/l+10% SVF.

The SPFM culture medium, without serum and without a vector protein is composed, either of RPMI 1640 BSM or of Williams E BSM, each containing 5.6 g/l of glucose+Na pyruvate: 1 mmole/l+dextran T2000: 10 mg/l+6 fatty acids: 7.6 µEq/l (see example 1)+gentamicin: 50 mg/l.

Figure 4:
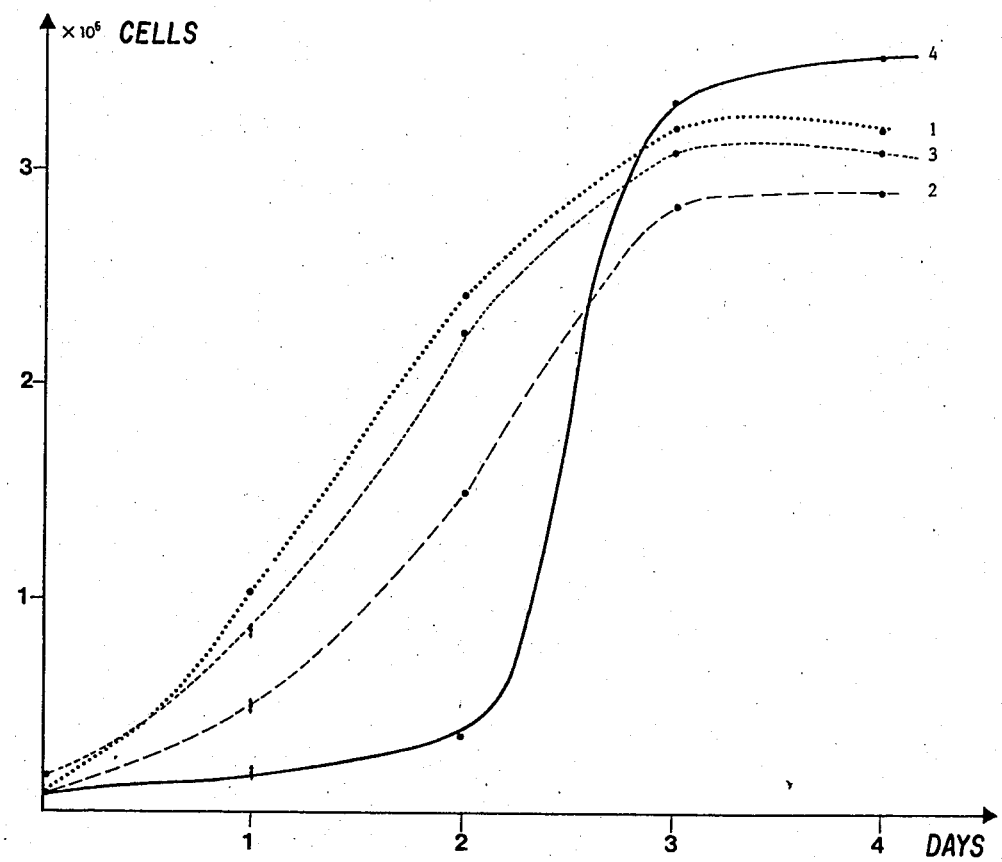

FIG. 4 shows the cell growth curves of the hybridoma Rota IV-21 in various media and various conditions (the cell counts are given in $10^6$ cells):

curve 1: growth of the Rota IV-21 hybridoma in Williams E BSM completed with glucose at 5.6 g/l+Na pyruvate: 1 mmole/l+gentamicin: 50 mg/l+10% SVF (medium 1); inoculation ratio: 100,000 cells/20 cm²; TMC: 3.23/0.1=32.3; TDPC: 72/32.3=2 h 14 min.

curve 2: represents the case of a sub-line of Rota IV-21 having previously already proliferated during 3 passages in the SPFM medium used below and which comprises Williams E BSM+gentamycin: 50 mg/l+glucose at 5.6 g/l+dextran T2000: 10 mg/l+fatty acids: 7.6 µEq+transferrin-iron: 5 mg/l+insulin: 1.25 mg/l+EGF: 5 µg/l (medium 2); inoculum: 100,000 cells/20 cm²; TMC: 2.85/0.1=28.5; TDPC: 72/28.5=2 h 32 min.

curve 3: same complete SPFM as medium 2, FH: 2 mg/l (medium 3) for the same sub-line adapted during 3 passages to growth in medium 2; inoculum: 150,000 cells/20 cm²; TMC: 3.21/0.15=21.4; TDPC: 72/21.4=3 h 22 min.

curve 4: same complete SPFM as in medium 3 but applied to a sub-line proliferating in the preceding passage in medium 1 containing serum; inoculum: 100,000 cells/20 cm²; TMC: 3.34/0.1=33.4; TDPC: 72/33.4=2 h 9 min.

In fluorescence microscopy the reaction is observed of the anti-rotavirus antibodies secreted by Rota IV-21 hybridomas growing in the SSM and SPFM culture media of the SSM line and of the SPFM sub-lines, against cells infected with rotavirus. In parallel are observed the corresponding controls where the infected cells are incubated in the respective fresh culture media.

The controls do not show any immunofluorescent histo-chemical reaction on the cells.

It is observed besides that the antibody production is very similar by comparing the three culture media without serum and without vector proteins SPFM, 2, 3 and 4 with respect to SSM containing 10% of serum.

It is deduced that the antibody production is effected in parallel with the ratio of proliferation of the hybridomas in these culture media and proportionately with the cell ratio at confluency at the end of growth of the culture (plateau phase at the beginning of the third day). Reduced to cell ratio, it is identical in all the media, whether in culture medium containing serum or in culture medium without serum and without vector protein.

By means of the invention it is now possible not only to maintain a hydridoma cell population in a serum-free medium but to cause it to proliferate in a medium containing neither serum, nor vector protein. This proliferation in this medium only occurs because it preserves for the hybridomas their capacity of anchorage to the substratum. Hence it is not necessary, as in the case of the culture technique proposed by Cleveland et al. (J: Immunol. Methods (1983), 56, 221–234), to proceed in a first phase with anchorage of the hybridoma cells to the substratum by means of a culture medium containing serum and to cause them to proliferate to result in a confluency of attached cells in euilibrium with suspended cells. In the process of Cleveland et al., at confluency, the medium containing serum can be replaced by the medium for maintaining the cells without serum in order to cause the production of antibodies by these cells into the culture medium without heterospecific immunoglobulins. Nonetheless, this medium does not permit in any way the growth by proliferation of the biomass of the cell strain. Hence the cells, whose antibody production can be limited to a limited life span of the line, are lost both for the propogation of the strain and for the increase of the monoclonal antibody production.

The serum-free culture medium according to the invention enables the maintenance and the proliferation of the line of the hybridoma which must pass through the cell anchorage and cell proliferation to result in a profitable monoclonal antibody production. The profitability is strongly increased by economies effected on the purification of the monoclonal antibody from the culture medium not containing foreign antibodies.

The example of hybridoma cell growth in the media 2 and 3 above has been carried out on a hybridoma sub-line which had already undergone three passages in medium 2. This demonstrates that the retentive effects of the serum cannot be invoked to explain the anchorage and then the proliferation of the hybridoma cells in the serum-free medium. In fact, the adaptation of the growth of a culture done previously in medium SSM (medium 1) to medium SPFM (medium 4) demonstrates the existence of a lag phase to ensure cell anchorage during 48 h before starting up of cell proliferation in the medium SPFM. In the case of SPFM cultures of media 2 and 3, the anchorage and cell proliferation progress simultaneously.

We claim:

1. Serum-free animal cell culture medium, characterized in that is consists essentially of:
   (a) a synthetic basal medium designed for animal cell culture;
   (b) 0.05 to 30 µeq/l of a mixture of the six fatty acids palmitic acid, cis-palmitoleic acid, stearic acid, cis-oleic acid, cis-linoleic acid and cis-linolenic acid or their esters, in the following proportions, relative to the free fatty acid:
   from 0.0155 to 24.0 µmole/l of palmitic acid;
   from 0.0058 to 9.0 µmole/l of cis-palmitoleic acid;
   from 0.0014 to 2.0 µmole/l of stearic acid;
   from 0.0067 to 10.0 µmole/l of cis-oleic acid;
   from 0.0178 to 27.0 µmole/l of cis-linolenic acid; and
   from 0.0028 to 4.0 µmole/l of cis-linolenic acid, adsorbed on
   (c) at least one water-soluble lipophile biopolymer present in an amount capable of ensuring the dissolution of the fatty acids or esters present in the medium.

2. Culture medium according to claim 1, wherein the mixture is of said six fatty acids are present therein in the free acid state.

3. Culture medium according to claim 1, wherein the synthetic basal medium is selected from the group consisting of:
Ham media
Waymouth MB 752/1 medium
RPMI 1629 or 1640 media
Eagle medium
modified Eagle media
Williams E medium
medium 199 and derived media of the types
MEM and
MEMα.

4. Culture medium according to claim 1, wherein said antibiotic has a wide spectrum.

5. Culture medium according to claim 1, wherein said antibiotic is gentamicin in the proportion of 25 to 100 mg/l.

6. Culture medium according to claim 1, wherein the water soluble lipophile biopolymer is constituted by lipid-free or not lipid-free albumin or by a dextran.

7. Culture medium according to claim 6, wherein the albumin is present in an amount of 2 to 6 g/l of culture medium.

8. Culture medium according to claim 6, wherein the dextran is present in an amount from 0.5 to 200 mg/l of culture medium.

9. Process for obtaining a cell line using the culture medium according to claim 1, which consists of:
(a) subjecting to enzymatic digestion the cellular product of a prior culture, to initiate one or several secondary culture(s),
(b) carrying out the one or more secondary culture(s) in the culture medium, and
(c) repeating steps (a) and (b) with the cellular product of the preceding step (b) as many times as necessary to preserve the cell line during the desired time.

10. Process for obtaining a cell line according to claim 9, wherein the cellular product results of a prior culture which as reached confluency.

11. Culture medium according to claim 1 further including an antibiotic in non-cytotoxic concentration throughout the passage of the culture.

12. Culture medium according to claim 1 further including at least one compound selected from hormones and growth factors.

13. Culture medium according to claim 12 further including an antibiotic in non-cytotoxic concentration throughout the passage of the culture.

14. A process for obtaining a cell line using the culture medium according to claim 13, which consists essentially of:

(a) suspending cells of a prior culture in the said culture medium;
(b) carrying out the culture of the cells in the said culture medium; and
(c) repeating steps (a) and (b) as many times as necessary to preserve the cell line during the desired time.

15. Process for the primary culture of rat liver epithelial cells using the culture medium according to claim 1, characterized in that it consists essentially of:
(1) taking up the tissue containing the cells to be cultivated and mincing it very finely, in a basal culture medium, not containing $Ca^{2+}$ and $Mg^{2+}$ ions, warmed (30°–37° C.), under aseptic conditions;
(2) after rinsing, in the basal medium not containing $Ca^{2+}$ and $Mg^{2+}$ ions, subjecting the tissue to a sequential enzymatic digestion,
(3) transferring the suspension of cells thus released into a basal culture medium, centrifuging while following in parallel the digestion of the remaining tissue in step 2,
(4) placing the centrifugation pellet in suspension in the culture medium then,
(5) inoculating the suspension so obtained on the culture substratum previously or simultaneously surfacted,
(6) incubating in an air-tight incubator, saturated with water vapour, in the presence of a nitrogen, oxygen, and carbon dioxide mixture at 76%:19%:5%, while renewing the culture medium periodically,
steps (3) to (6) being repeated on the different fractions of dissociated desired cells, obtained sequentially at step (2), using each time a new culture substratum.

16. A process according to claim 15 wherein, in step (4), the culture medium contains a surface coating agent for the culture substratum.

17. Process of primary culture of rat liver epithelial cells according to claim 15, characterized in that the enzymatic digestion is carried out by means of collagenase or trypsin.

18. Process of primary culture of rat liver epithelial cells according to claim 15, characterized in that the surfacting of the substratum is carried out by means of serum, collagen, polylysine or fibronectine.

19. Process according to claim 18, wherein the surface coating agent of the substratum is fetal calf serum, newborn calf serum or fibronectin.

20. Process of primary culture of rat liver epithelial cells according to claim 15, wherein the basal culture medium is that used in the preparation of the culture medium of step (4).

* * * * *